United States Patent [19]

Mabry et al.

[11] Patent Number: 4,550,185

[45] Date of Patent: Oct. 29, 1985

[54] PROCESS FOR MAKING TETRAHYDROFURAN AND 1,4-BUTANEDIOL USING PD/RE HYDROGENATION CATALYST

[75] Inventors: Melinda A. Mabry, Wilmington; William W. Prichard, Hockessin; Stanislaw B. Ziemecki, Wilmington, all of Del.

[73] Assignee: E. I. Du Pont de Nemours and Company, Wilmington, Del.

[21] Appl. No.: 564,372

[22] Filed: Dec. 22, 1983

[51] Int. Cl.[4] ............................................. C07D 307/08
[52] U.S. Cl. .................................... 549/508; 568/864; 502/325
[58] Field of Search ........................................ 549/508

[56] References Cited

U.S. PATENT DOCUMENTS

| | | | |
|---|---|---|---|
| 3,113,138 | 12/1963 | Franko-Filinasie et al. | 260/343.6 |
| 3,370,067 | 2/1968 | Johnson | 260/346.1 |
| 3,759,841 | 9/1973 | Wilhelm | 252/441 |
| 3,957,827 | 5/1976 | Lyons | 260/343.3 R |
| 4,155,919 | 5/1979 | Ramioulle et al. | 260/346.11 |
| 4,231,943 | 11/1980 | Paradis et al. | 260/346.75 |
| 4,244,878 | 1/1981 | McDermott | 260/346.75 |
| 4,251,390 | 7/1980 | Brandt | 362/311 |
| 4,283,288 | 8/1981 | Udovich et al. | 252/437 |
| 4,342,644 | 8/1978 | Mauldin et al. | 208/139 |

FOREIGN PATENT DOCUMENTS

| | | |
|---|---|---|
| 1070711 | 5/1975 | Canada . |
| 2715667 | 4/1977 | Fed. Rep. of Germany . |
| 43-68369 | 9/1968 | Japan . |
| 3243974 | 8/1984 | Japan . |
| 1534232 | 2/1977 | United Kingdom . |

*Primary Examiner*—Richard L. Raymond
*Attorney, Agent, or Firm*—James A. Costello

[57] ABSTRACT

Palladium/rhenium-on-carbon catalyst; a method employing said catalyst to produce tetrahydrofuran, 1,4-butanediol or mixtures thereof in selectable ratios from a number of starting reactants; and a method for making the Pd/Re/C catalyst.

30 Claims, No Drawings

PROCESS FOR MAKING TETRAHYDROFURAN AND 1,4-BUTANEDIOL USING PD/RE HYDROGENATION CATALYST

BACKGROUND OF THE INVENTION

1. Field of the Invention

One aspect of this invention concerns making tetrahydrofuran, 1,4-butanediol or mixtures thereof by hydrogenating a variety of hydrogenatable precursors such as maleic acid, maleic anhydride, fumaric acid, succinic acid, malic acid, dimethyl succinate, γ-butyrolactone or mixtures thereof. These precursors can be described as dicarboxylic acids, dicarboxylic acid esters, lactones or mixtures of said acids, esteres, lactones and/or anhydrides. Another aspect of this invention concerns a continuous catalytic process for making tetrahydrofuran, 1,4-butanediol or mixtures thereof from a normal $C_4$ hydrocarbon such as n-butane. The particular Pd/Re/C catalyst employed for these processes is another aspect of this invention as is the preferred method for making the catalyst.

2. State of the Art

There are numerous methods disclosed in the art for making tetrahydrofuran and 1,4-butanediol. There are publications relating to the hydrogenation of maleic acid or maleic anhydride that also describe various attempts to maximize product yields. For instance, in this regard see: U.S. Pat. No. 4,155,919, U.S. Pat. No. 3,957,827, U.S. Pat. No. 3,370,067 and U.S. Pat. No. 3,113,138; Japanese Patent Publications Nos. 32439/74 and 43683/69; German Patent Publications Nos. 2,519,817 and 2,715,667; and British Pat. No. 1,534,232. These publications describe catalytic processes for making maleic acid/maleic anhydride; U.S. Pat. No. 4,251,390, U.S. Pat. No. 4,231,943, U.S. Pat. No. 4,244,878 and U.S. Pat. No. 4,283,288.

French Pat. No. 2,505,819 discloses hydrogenation reactions employing supported Rd/Re catalysts. Although the catalysts can be made by sequential deposition of Pd and Re metal, no intermediate reduction is disclosed.

The subject of this invention concerns optimization of the process for making tetrahydrofuran and 1,4-butanediol. The described methods employ a selected catalyst to produce high yields of tetrahydrofuran and 1,4-butanediol with high productivity. The methods proceed from dicarboxylic acid or dicarboxylic acid ester starting reactants. The methods of this invention are characterized in that they can be oriented, as desired, toward production of high ratios of tetrahydrofuran to 1,4-butanediol or vice versa.

SUMMARY OF THE INVENTION

This invention concerns a composite catalyst of palladium and rhenium on a carbon support. The catalyst comprises from about 0.5% to 10% of palladium and about 1% to 10% of rhenium by weight. A preferred catalyst contains about 1 to 6% of Pd and 3 to 6% of Re and an especially preferred catalyst contains about 3% of Pd and 3% of Re.

The Pd/Re/C catalyst of this invention comprises Pd in the form of crystallites having an average size of about 10 to 25 nm and Re in the form of a highly dispersed phase of crystallites less than about 2.5 nm and preferably less than 1.5 nm in size. Pd crystallite sizes have been determined by $H_2/O_2$ titration, and Re crystallite sizes by scanning transmission electron microscopy (STEM). The highly dispersed Re crystallites are too small to be detected by X-ray diffraction or by STEM.

This invention also concerns a method for making said catalyst comprising, in sequence, the steps of:
(i) impregnating the carbon support with a source of palladium in solution and removing the solvent,
(ii) heating the palladium impregnated carbon at a temperature of about 150° C. to 550° C., preferably about 200° C. to 300° C., under reducing conditions, usually for about 2 to 5 hours,
(iii) applying to the palladium impregnated carbon a source of rhenium that is in solution, and removing the solvent to form the Pd/Re/C catalyst.

It is preferred to heat the Pd/Re/C catalyst of step (iii) at a temperature of about 150° C. to 550° C., preferably about 200° C. to 300° C., under reducing conditions, usually for about 2 to 5 hours. This reduction can be carried out immediately after step (iii) or it can be done in the hydrogenator just before the reaction is carried out or simultaneously with the inception of the reaction.

It is preferred to have a Group IA or IIA metal such as potassium, sodium, lithium, calcium, or magnesium present during the catalyst synthesis. Preferred amounts are about 0.1 to 1 mole percent based on the number of moles of carbon in the support. Preferred supports have a surface area in excess of about 650 $m^2/g$ and most preferably in excess of about 900 $m^2/g$.

This invention also concerns a process for the selective production of tetrahydrofuran, 1,4-butanediol or mixtures thereof by the hydrogenation of hydrogenatable precursors such as maleic anhydride, maleic acid, fumaric acid, succinic acid, malic acid, succinic esters such as dimethyl succinate, γ-butyrolactone or mixtures of two or more thereof in an aqueous or organic solvent medium at a reaction temperature of about 130° C. to 285° C., a hydrogen pressure of about 300 psig (2 MPa) to 5000 psig (35 MPa), a hydrogen spacetime of about 1 to 10 minutes, and a contact time of about 0.5 to 7 hours in the presence of the carbon-supported palladium-rhenium catalyst described above. Representative organic media include dioxane, γ-butyrolactone, and the like. The preferred precursors are maleic acid and maleic anhydride.

The catalyst of this invention provides (a) substantially 100% conversion of the precursor(s), (b) high selectivity to and yield of the THF/BDO product, and (c) the advantage of being able to control the product ratio of THF/BDO by varying the temperature, the contact time and/or the hydrogen spacetime within the described operating ranges so that, generally, the higher the temperature, the longer the contact time, and/or the higher the hydrogen spacetime, the higher the ratio of THF to BDO, and vice versa. Hydrogen spacetime is defined as the reaction volume divided by the hydrogen flow rate under reaction conditions.

This invention also concerns a continuous process for the production of tetrahydrofuran, 1,4-butanediol or a mixture thereof from a normal $C_4$ hydrocarbon or an aromatic hydrocarbon comprising:
(i) oxidizing the hydrocarbon to form maleic anhydride,
(ii) collecting the maleic anhydride produced in step (i) in an aqueous solution, and
(iii) reacting the aqueous solution of maleic acid with hydrogen in the presence of the Pd/Re/C catalyst of this invention under the described conditions.

It is the essentially complete conversion of maleic acid and the high selectivity to and yield of THF/BDO in an aqueous medium obtained with the carbon-supported palladium-rhenium catalyst that makes this continuous process efficient and useful.

DETAILS OF THE INVENTION

The Catalyst

One method for making the catalyst comprises (a) applying a solution of a palladium compound to a carbon support and removing the solvent; (b) heating the carbon impregnated with the palladium compound produced in (a) at a temperature of about 150° C. to 550° C., preferably about 200° C. to 300° C., under reducing conditions, cooling the carbon-supported palladium composite (Pd/C) produced in (b), and (c) applying a solution of rhenium compound to this composite and removing the solvent.

It is preferred to heat the Pd/C impregnated with the rhenium compound produced in step (c) above at a temperature of about 150° C. to 550° C., preferably about 200° C. to 300° C., under reducing conditions for about 2 to 5 hours. This can be done immediately following step (c), or it can be done in the hydrogenation apparatus just before the reaction is carried out or simultaneously with the inception of the reaction.

Preferably, preparation of the Pd/Re/C catalyst is carried out in the presence of Group IA or IIA metals such as potassium, sodium, lithium, calcium or magnesium. The latter may be present in the carbon as obtained or may be added, if absent, by impregnating the carbon support with a solution of a Group IA or IIA metal compound, e.g., LiCl, NaCl, KCl, KOH, NaOH, $CaCl_2$, or $MgCl_2.6H_2O$. It is believed that the group IA or IIA metal has a beneficial effect on the catalyst microstructure.

Alternatively, the Group IA or Group IIA metal can be added with the palladium by adding the Group IA or Group IIA metal compound to the solution of the palladium compound or by using a palladium compound that also contains the Group IA or Group IIA metal, e.g., $K_2PdCl_4$ or $Na_2PdCl_4$. It is preferred to add the Group IA or Group IIA metal to the carbon support and to calcine the impregnated carbon at temperatures in the range of about 200° C. to 400° C. for about two to six hours before impregnating the carbon support with the source of palladium.

The solutions of palladium compound and rhenium compound can be applied to the carbon by immersing or suspending the support material in the solution or by spraying the solution onto the carbon. The solution containing the palladium compound is typically an acidic aqueous medium containing HCl and an amount of palladium compound to yield a catalyst product with the requisite amount of palladium. The palladium compound is typically $PdCl_2$ but can also be a palladium compound such a nitrate, carbonate, carboxylate, acetate, acetyl acetonate, or amine. The solution containing the rhenium compound is typically an aqueous one containing an amount of rhenium compound to yield a catalyst product with the requisite amount of rhenium. The rhenium compound is typically $Re_2O_7$ but can be a perrhenate of ammonium or of an alkali metal.

By heating under reducing conditions is meant heating in a reducing environment, preferably hydrogen. Typically, the sample has been reduced by first heating in flowing He at 150° C. for about one hour, then heating at 150° in flowing He/$H_2$ (50:50 mole ratio) for about one hour and finally heating at 150° to 550° C. in flowing He/$H_2$ (50:50 mole ratio) for up to about 3 hours.

When a Group IA or Group IIA metal is present in the carbon support during catalyst preparation, large (about 0.2 μm) crystallites of the salts of $ReO_4^-$ are present in the catalyst as observed by X-ray diffraction and scanning transmission electron microscopy. If this catalyst is further exposed to reducing conditions, e.g., during the hydrogenation of maleic acid, and then reexamined, no salts of $ReO_4^-$ or any phase containing a Group IA or Group IIA salt can be detected. However, the catalyst is still comprised of the Pd and Re crystallites described herein.

Catalytic Method

When the starting reactant is a normal $C_4$ hydrocarbon, the process proceeds without the need for equipment, energy and time usually required to isolate and purify the maleic anhydride as described in prior art hydrogenations. A typical method for carrying out the process comprises (a) reacting n-butane or benzene in an oxygen-containing gas in the presence of a vanadium/phosphorus mixed oxide catalyst to oxidize in the vapor phase the n-butane to maleic anhydride, (b) collecting the maleic anhydride by a water quench to produce maleic acid in an aqueous solution at a concentration of about 40 weight percent, and (c) reacting the solution obtained in (b) with hydrogen in the presence of the Pd/Re/C hydrogenation catalyst.

Preferably, oxidation step (a) is operated at a temperature of about 300° to 600° C. and a pressure of about 0.5 to 20 atmospheres (50 to 2000 kPa) and hydrogenation step (c) is run at a temperature of about 150° C. to 275° C., and a hydrogen pressure of about 300 psig (2 MPa) to 5000 psig (35 MPa).

The liquid phase hydrogenation of this invention can be run using conventional apparatus and techniques in a stirred-tank reactor or in a fixed-bed reactor. Hydrogen is fed continuously, generally in considerable stoichiometric excess with no inert diluent gases. Unreacted hydrogen can be returned to the reactor as a recycle stream. The precursor solution, e.g., maleic acid solution, is fed continuously at concentrations ranging from dilute solutions to near the maximum solubility level, typically about 30 to 40 weight percent. The catalyst carbon support is about 200 mesh particle size for use in the stirred-tank reactor or of larger support granules ⅛″ (0.64 cm) through 60 mesh for use in the fixed-bed reactor. The amount of catalyst required will vary widely and is dependent upon a number of factors such as reactor size and design, contact time and the like. For example, for a 60 cc-volume reactor, 25 g of the preferred catalyst, 3% Pd/3% Re/C is used.

The following Examples illustrate the invention. Temperatures are in degrees Celsius unless otherwise stated. Unless stated to the contrary, all the hydrogenation experiments were run in a reactor having a 0.5″ (1.27 cm) diameter and a length of 30″ (76 cm). The reactor was constructed from BWG 20, ½″ Hastelloy C tubing, wall thickness=0.035″ (0.09 cm), I.D.=0.430″ (1.1 cm). The reactor volume was calculated based on the catalyst packed volume. For all the Examples, the packed bed length was 25″ (63 cm). Void volume was filled with inert silicon carbide. The resultant catalyst reaction volume was calculated to be 59.49 cc which is the value used for determining the superficial reaction residence time, i.e., contact time.

The reactor was operated in a co-current, upflow mode. Liquid maleic acid, or any of the other precursor feeds, and hydrogen were metered separately and then introduced into a mixing tee at the base of the reactor. Intimate mixing, as well as preheating, was accomplished in the inert, packed bed section. Products, as well as excess hydrogen, discharged through a valve in which the pressure was let down to atmospheric pressure from the reaction pressure. The liquid collected was the bulk of product containing tetrahdrofuran (THF) and 1,4-butanediol (BDO) with minor amounts of by-product. The reaction vapor stream was passed through a series of vapor/liquid disengagement vessels: the first was at room temperature, followed by a water-/ice trap, followed by two (in series) dry ice/acetone traps. The product collected was primarily THF with minor amounts of mono-alcohols and butyrolactone. These traps were employed because of the difficulty of small scale liquid/vapor disengagement.

Unless otherwise stated, the maleic acid feed was prepared by adding 500 g of certified grade maleic anhydride (Fisher Scientific Co.) to 1190 g of distilled water. The hydrogen was from 99%+ purity hydrogen cylinders and was compressed to a reaction pressure of about 2500 psig (17 MPa). The hydrogen feed rate was 1000 cc/min (STP) which is equivalent to a hydrogen spacetime of 6 minutes at reaction conditions, i.e., 2500 psig (17 MPa) and 200° C. Unless otherwise stated, the hydrogen spacetime was 6 minutes. The catalyst was particulate and less than 20 mesh in size. The unit in which the "Space Time Yield" is expressed in all Table headings and Examples is $$\frac{g \ Product}{kg \ Cat - hr.}$$

EXAMPLE 1

A 3 weight percent Pd/3 weight percent Re/carbon-supported catalyst (3% Pd/3% Re/C) was prepared in the following manner. Calgon PCB 12×30 carbon was calcined at 200° for two hours, then at 400° for two hours. This treated carbon had a surface area of 1000 to 1300 $m^2$/g with pore volume of 0.6 cc/g. A sequential deposition of Pd and Re onto the treated carbon was made as follows: 50 g of treated carbon was added to a solution of 2.5 g of $PdCl_2$ in 10 ml of concentrated HCl and 80 ml of distilled water. After three hours at room temperature with occasional stirring, the slurry was dried for eighteen hours at 110°.

The sample was reduced by being first heated to 150° in flowing He (1000 cc/min) for one hour, then heated at 150° in flowing $He/H_2$ (50:50 mol ratio, 1000 cc/min) for one hour, and finally heated at 300° in flowing $He/H_2$ (50:50 mol ratio, 1000 cc/min) for 3 hours. The sample was cooled rapidly to 50° in the $He/H_2$ atmosphere. Nitrogen was introduced while the sample cooled to ambient temperature. After thirty minutes in flowing $N_2$, the sample was passivated at room temperature by introduction of flowing 1:99 (mol ratio) $O_2/N_2$ for two hours.

Next, 5 g of $Re_2O_7$ was added to 50 ml of distilled water and then 19.7 ml of this solution and 70 ml of distilled water were delivered to a 1000 ml flask along with 50 g of the Pd/C catalyst. After three hours at room temperature with occasional stirring, the slurry was dried, reduced, and passivated in the manner described for the Pd/C catalyst. The resultant material was the 3% Pd/3% Re/C catalyst.

The Pd/Re/C catalyst prepared in this Example was examined by X-ray diffraction, scanning transmission electron microscopy, and $H_2/O_2$ titration and found to have palladium crystallites of average size to about 150 Å to 200 Å (15 to 20 nm). The particles of rhenium were below the size at which they could be detected by X-ray diffraction or by scanning transmission electron microscopy. It is estimated, therefore, that rhenium particles sizes were below about 25 Å (2.5 nm).

By the described microscopy and crystallography techniques, $KReO_4$ crystallites with an average size of about 0.2 $\mu$m were detected. Microscopy observations showed that the highly dispersed rhenium phase of small crystallites discussed above is in contact with some palladium crystallites. The carbon support used in the preparation of this catalyst contained 0.36 mole percent of K.

EXAMPLES 2 TO 14

The 3% Pd/3% Re/C catalyst prepared as described in Example 1 was charged to a 0.5" diameter reactor. The maleic acid feed rate was adjusted to give contact times of from about 0.9 hours to 5.5 hours (for example, a maleic acid feed rate of 0.5 cc/min gives a reaction or contact time of 2.0 hours) and the hydrogen flow rate adjusted to give a hydrogen spacetime of either 3 or 6 minutes. The hydrogenation reaction was carried out at reaction temperatures of 175°, 180°, 190°, 200°, 215°, and 225°. The reaction product was sampled continuously. The distribution of product THF and BDO and by-product mono-alcohols such as butanol, propanol, etc., and the intermediate γ-butyrolactone in mol percent based on carbon species are shown in Table 1 for the various reaction conditions. These are averages of several measurements taken after steady-state conditions were reached.

No detectable amount of maleic acid was found indicating that substantially all was converted. Therefore, the mol percentage shown is the selectivity as well as the yield of the particular component. Also shown is the space-time yield. Space time yield is that quantity of product obtained per unit time per unit weight of metal catalyst charged. The results show that there is high selectively to and yield of THF/BDO and that the THF/BDO product ratio increases as the temperature increases, as the contact time increases and/or as the hydrogen space time increases and that the product ratio can be adjusted over a range from substantially only BDO to substantially only THF.

TABLE 1

| Example | Temperature °C. | Contact Time (Hrs) | $H_2$ Space Time (Min) | Product// By-Product THF/BDO// Aloh[1]/Btyl[2] (Mol Percent) | Space Time Yield |
|---|---|---|---|---|---|
| 2 | 175 | 3.8 | 6 | 80/14//5/1 | 146 |
| 3 | 175 | 5.5 | 6 | 85/0//15/0 | 93 |
| 4 | 180 | 2.0 | 3 | 13/79//8/0 | 325 |
| 5 | 180 | 3.8 | 6 | 90/2//8/0 | 140 |
| 6 | 180 | 5.5 | 6 | 85/0//15/0 | 94 |
| 7 | 190 | 2.0 | 3 | 50/40//10/0 | 290 |
| 8 | 190 | 2.2 | 6 | 72/17//7/4 | 236 |
| 9 | 190 | 3.7 | 6 | 88/1//11/0 | 134 |
| 10 | 190 | 4.9 | 6 | 84/0//16/0 | 103 |
| 11 | 200 | 2.0 | 3 | 70/20//10/0 | 275 |
| 12 | 200 | 2.2 | 6 | 85/5//10/0 | 251 |
| 13 | 215 | 2.0 | 3 | 85/1//14/0 | 250 |

TABLE 1-continued

| Example | Temperature °C. | Contact Time (Hrs) | H₂ Space Time (Min) | Product// By-Product THF/BDO// Aloh[1]/Btyl[2] (Mol Percent) | Space Time Yield |
|---|---|---|---|---|---|
| 14 | 225 | 0.9 | 6 | 83/4//12/1 | 429 |

[1]Total monoalcohols:n-butanol, n-propanol.
[2]γ-Butyrolactone.

EXAMPLES 15 TO 18

A 1% Pd/3% Re/C catalyst was prepared using the method described in Example 1 except that the amount of PdCl₂ was ⅓ of that noted and the highest temperature of the reduction following Pd deposition was 350° and the highest temperature of the reduction following Re deposition was 150°.

Hydrogenation was carried out as described in Examples 2 to 14 with a reaction temperature of 180°. The maleic acid flow rate was adjusted so that the contact time varied from 2.1 to 3.5 hours. The results given in Table 2 show that the THF/BDO product ratio increased as contact time increased.

TABLE 2

| Example | Reaction Contact Time (Hrs) | Product//By-Product THF/BDO// Aloh[1]/Btyl[2] (Mol Percent) | Space Time Yield |
|---|---|---|---|
| 15 | 2.1 | 50/20//4/24 | 200 |
| 16 | 3.3 | 64/30//6/0 | 174 |
| 17 | 3.4 | 75/19//6/0 | 164 |
| 18 | 3.5 | 85/9//6/0 | 156 |

[1]Total monoalcohols:n-butanol, n-propanol.
[2]γ-Butyrolactone.

EXAMPLES 19 TO 24

A 3% Pd/1% Re/C catalyst was prepared by the method described in Example 1 except that the amount of Re₂O₇ was ⅓ of that noted in Example 1. Hydrogenation was carried out as in Examples 2 to 14 with various reaction temperatures and reaction contact times. The results given in Table 3 show that increased reaction temperature and/or increased reaction contact times result in higher THF/BDO. No measurable amount of maleic acid was found, indicating essentially complete conversion.

TABLE 3

| Example | Reaction Temperature °C. | Reaction Contact Time (Hrs) | Product//By-product THF/BDO//Aloh[1] /Btyl[2]/Suac[3] (Mol Percent) | Space Time Yield |
|---|---|---|---|---|
| 19 | 180 | 2.0 | 18/2//2/45/33 | 60 |
| 20 | 180 | 5.9 | 83/1//10/5/1 | 90 |
| 21 | 200 | 3.5 | 43/3//5/39/10 | 80 |
| 22 | 215 | 3.5 | 59/1//7/29/4 | 100 |
| 23 | 215 | 4.0 | 73/1//12/10/4 | 110 |
| 24 | 225 | 3.3 | 66/1//11/19/3 | 115 |

[1]Total monoalcohols:n-butanol, n-propanol.
[2]γ-Butyrolactone.
[3]Succinic acid.

EXAMPLE 25

A 10% Pd/3% Re/C catalyst was prepared by the method described in Example 1 except the amount of PdCl₂ was 10/3 of that noted in Example 1. Dimethyl succinate (53.76 g) and 6.0 g of water were placed in a pressure vessel and contacted with 30 g of the 10% Pd/3% Re/C catalyst at a hydrogen pressure of 2500 psig and a temperature of 285° for 2 hours. The reaction product based on the carbon species showed 62.2 mol percent of THF, 18.6 mol percent of butanol, 4.7 mol percent of propanol and 14.5 mol percent of γ-butyrolactone.

EXAMPLES 26 AND 27

A 3% Pd/3% Re/C catalyst was prepared by the method described in Example 1 except that the highest temperature of both reduction steps was 200° instead of 300°. Hydrogenation was carried out as described in Examples 2 to 14 but with the reaction conditions given in Table 4. The results show that longer contact time results in higher THF to BDO ratios.

TABLE 4

| Example | Temperature °C. | Contact Time (Hrs) | Product// By-product THF/BDO// Aloh[1]/ Btyl[2]/Suac[3] (Mol Percent) | Space Time Yield |
|---|---|---|---|---|
| 26 | 180 | 2.0 | 70/21//7/1/1 | 264 |
| 27 | 180 | 3.3 | 82/7//11/0/0 | 151 |

[1]Total monoalcohols:n-butanol, n-propanol.
[2]γ-Butyrolactone.
[3]Succinic acid.

EXAMPLES 28 TO 32

A 3% Pd/3% Re/C catalyst was prepared by the method described in Example 1 except that the reaction step after the palladium compound deposition was carried out at a highest temperature of 500° instead of 300°. Hydrogenation was carried out as in Examples 2 to 14 but with the reaction conditions given in Table 5. The results demonstrate the advantages of the catalyst of this invention.

TABLE 5

| Example | Temperature °C. | Contact Time (Hrs) | Product// By-product THF/BDO// Aloh[1]/ Btyl[2]/Suac[3] (Mol Percent) | Space Time Yield |
|---|---|---|---|---|
| 28 | 180 | 2.1 | 45/23//5/19/8 | 212 |
| 29 | 180 | 3.2 | 86/7//6/9/1 | 174 |
| 30 | 180 | 3.4 | 76/17//5/1/1 | 170 |
| 31 | 190 | 3.3 | 90/1//9/0/0 | 161 |
| 32 | 190 | 3.4 | 86/4//9/0/1 | 158 |

[1]Total monoalcohols:n-butanol, n-propanol.
[2]γ-Butyrolactone.
[3]Succinic acid.

EXAMPLE 33

A 6% Pd/3% Re/C catalyst was prepared by the method described in Example 1 except that the amount of PdCl₂ used was twice that noted in Example 1. Hydrogenation was carried out as described in Examples 2 to 14. At a reaction temperature of 180° and a contact time of 2.1 hours, the product//by-product distribution in mol percent was THF-67/BDO-19//monoalcohols-8/γ-butyrolactone-5/succinic acid-1 and the spacetime yield was 239.

EXAMPLE 34

A 6% Pd/6% Re/C catalyst was preared by the method described in Example 1 except that the amount of PdCl₂ used was twice that noted in Example 1 and fraction but no metallic Re could be detected. The microstructure of the catalyst of Comparison B wherein Re and then Pd were deposited sequentially comprised Pd crystallites of only about 8 nm in average size and Re in large crystallites of about 50 nm in average size before use. In addition, contact between Pd and Re phases was not evident. After use, the Pd and Re phases were amorphous and hence not detected by X-ray diffraction.

The reaction temperatures, contact times and product//by-product//feed distributions are shown in Table 6. It will be observed that the catalyst of this invention provides complete maleic acid conversion and high selectivity to THF/BDO, while the catalysts of Comparisons A and B give incomplete conversions and poor selectivities.

TABLE 6

| | Temperature | Contact Time (Hrs) | Product//By-product/Unreacted Maleic Acid THF/BDO//Aloh[1]/Btyl[2]/Suac[3]//Maleic (Mol Percent) | Space Time Yield |
|---|---|---|---|---|
| Example 37 | 215 | 1.5 | 43/46//9/2/0//0 | 390 |
| Comparison A | 208 | 1.5 | 5/15//5/45/25//5 | 129 |
| Comparison B | 215 | 1.5 | 5/20//5/50/15//5 | 163 |

[1] Total monoalcohols: n-butanol, n-propanol.
[2] γ-Butyrolactone.
[3] Succinic acid.

EXAMPLES 38 TO 47

The following Examples were carried out with the catalyst of Example 1 to demonstrate use of different feed materials, different strength solutions, and water and organic solvents. The feed solutions, reaction conditions and results are shown in Tables 7 and 8. The hydrogen spacetime was 6 minutes in all cases.

TABLE 7

| Example | Feed (Solution Strength in weight Percent) | Temp (°C.) | Contact Time (Hrs) | Space Time Yield |
|---|---|---|---|---|
| 38 | Aqueous Malic Acid(8) | 200 | 4.4 | 93 |
| 39 | Aqueous Malic Acid(8) | 230 | 4.4 | 73 |
| 40 | Aqueous Succinic Acid(5) | 200 | 2.2 | 29 |
| 41 | Aqueous Maleic Acid(35) | 200 | 4.5 | 103 |
| 42 | Aqueous Maleic Acid(5) | 170 | 2.2 | 225 |
| 43 | Maleic Anhydride in Dioxane(35) | 180 | 7.0 | 103 |
| 44 | Maleic Anhydride in Dioxane(35) | 180 | 4.1 | 123 |
| 45 | Maleic Anhydride in Dioxane(35) | 200 | 3.9 | 138 |
| 46 | Maleic Anhydride in Dioxane(35) | 230 | 1.6 | 325 |
| 47 | Maleic Anhydride in γ-butyrolactone(35) | 180 | 3.2 | 150 |

TABLE 8

PRODUCT//BY-PRODUCT DISTRIBUTION

| Example | THF | BDO // | Alcohol | γButyrolactone | Succinic Acid | Unconverted Precursor |
|---|---|---|---|---|---|---|
| 38 | 58 | 21 | 21 | 0 | 0 | 0 |
| 39 | 66 | 0 | 24 | 0 | 0 | 0 |
| 40 | 72 | 0 | 28 | 0 | 0 | 0 |
| 41 | 70 | 5 | 25 | 0 | 0 | 0 |
| 42 | 45 | 40 | 4 | 10 | 1 | 11 |
| 43 | 52 | 37 | 11 | 0 | 0 | 0 |
| 44 | 23 | 36 | 3 | 34 | 4 | 38 |
| 45 | 82 | 0 | 17 | 1 | 0 | 1 |
| 46 | 80 | 0 | 20 | 0 | 0 | 0 |
| 47 | 31 | 21 | 1 | 44 | 2 | 1 |

COMPARISON C

Example 1 was repeated except that the carbon support was leached with HCl to lower the level of K to less than about 0.001 mole percent prior to the deposition of the Pd and Re. The catalyst microstructure was altered in that the Pd crystallite size, as determined by $H_2/O_2$ titration, was only about 5 nm. Hydrogenation by the general procedure of Examples 2 to 14 at a temperature of 180° C. and with hold-up times of 2 hours and 2.2 hours, respectively, gave a selectivity of 13/79 (THF/BDO) and a spacetime yield of 325 with the catalyst of Example 1 versus a selectivity of 33/19 (THF/BDO) and a spacetime yield of 210 with the catalyst from which K was leached.

EXAMPLE 48

A 3 weight percent Pd/3 weight percent Re/carbon-supported catalyst in which 0.5 mole percent sodium was added to the potassium-leached carbon was prepared in the following manner. Calgon ® PCB 12×30 carbon was calcined at 200° C. for two hours then at 400° C. for two hours. Ash and fines were separated by screening on a 20 mesh sieve. Then 200 grams of the resultant carbon was added to 4 liters of 1 M HCl. The slurry was left standing for 24 hours. The carbon was then collected on a fritted funnel and washed with 4 liters of distilled water. The acid wash was repeated, and the carbon was then dried at 110° C. for 18 hours. The yield was 190.3 grams of potassium-leached carbon. The potassium-free carbon (50.0 g) was added to a solution of 1.3 g of NaCl in 70 ml of distilled water. After three hours at room temperature with occasional stirring, the slurry was dried at 110° C. for 18 hours. The carbon-with-Na was added to a solution of 2.5 g of $PdCl_2$ and 10 ml of conc HCl in 65 ml of distilled water. After three hours at room temperature with occasional stirring, the slurry was dried at 110° C. for 18 hours. The Pd/C sample was then heated for one hour at 150° C. in helium at 100 cc/min, then one hour at 150° C. in helium/hydrogen at 100 cc/min each, and finally, for three hours at 300° C. in the same helium/hydrogen atmosphere. After cooling in flowing helium/hydrogen, the solid was passivated with 1.5% oxygen in nitrogen for 18 hours.

The passivated Pd/carbon solid (48.3 g) was added to a solution of 19 ml of 0.2M $Re_2O_7$ in 51 ml of water. After three hours at room temperature with occasional stirring, the slurry was dried at 110° C. for 18 hours. The sample was then reduced and passivated as described above; 47.8 grams of Pd/Re/C catalyst were produced.

the amount of $Re_2O_7$ used was also twice as much. Hydrogenation was carried out as in Examples 2 to 14. At a reaction temperature of 180° and a contact time of 2.0 hours, the product//by-product distribution in mol percent was THF-40/BDO-50//monoalcohols-9/$\gamma$-butyrolactone-1 and the spacetime yield was 300.

EXAMPLE 35

The catalyst of Example 1 was used in a hydrogenation demonstration identical to that of Examples 2 to 14 except that the feed was fumaric acid in aqueous solution at a concentration of 9 weight percent. The reaction temperature was 180° and the reaction time 2.0 hours. The THF/BDO//monoalcohol/Btyl distribution in mol percent was 19/71//8/2. The spacetime yield was 72.

EXAMPLE 36

A continuous process for producing THF/BDO from n-butane via an unisolated maleic acid intermediate is as follows. Pre-activated V/P/$O_x$: 3 atom percent in about 2 weight percent $SiO_2$ catalyst in the form of $\frac{1}{8}$" diameter pellets and weighing about 70 g was charged into a vertical 1" diameter, 12" high, no. 316 stainless steel fixed-bed reactor which was heated in a fluidized sand bath to achieve temperature control. This reactor was connected so as to allow on-line transport of (1) the feed stream comprising about 1.5 percent of n-butane in air from a feed mainfold through a preheater coil contained in the sand bath and then into the bottom of the reactor in order to contact the catalyst bed, and (2) the product stream through an exiting line heated at a temperature somewhat over 200° (to avoid deposition of maleic anhydride) and then to a splitter that passed about 80 percent of the effluent gases through water to absorb out maleic anhydride for subsequent hydrogenation.

The remaining portion of the product stream was transported through a heated line to dual gas chromatographic (GC) facilities for product analyses. Insertion of a heated back-pressure valve in the exit line ahead of the GC train allowed operation of this system from atmospheric pressure (100 kPa) to a maximum of about 125 psia (870 kPa). Operating temperatures were in the range of 380° to 450° and contact times, as expressed at standard temperature and pressure, in the range of 1 to 7 seconds. The analytrical train allowed determination of $N_2$, $O_2$, CO, $CO_2$, $H_2O$, n-butane, maleic anhydride, ethylene, furan, methyl ethyl ketone, acetic acid, and acrylic acid. The maleic acid solution was colorless.

Hydrogenation of the crude maleic acid intermediate was carried out as described in Example 2 to 14 using the 3% Pd/3% Re/C catalyst of Example 1. The maleic acid concentration was 33 weight percent and the maleic acid feed rate was 0.5 cc/min corresponding to a contact time of 2 hours. The reaction temperature was 200°. The product//by-product (THF/BDO//monoalcohol) distribution in mole percent was 30/58//12. The spacetime yield was 280.

EXAMPLE 37 AND COMPARISONS A AND B

This Example and the Comparisons were carried out to demonstrate the activity of a catalyst of this invention (Example 37) versus the lesser activities of two catalysts not of this invention (Examples A and B). In the Example and the Comparisons, the catalyst comprised 3 weight percent of Pd and 3 weight percent of Re supported on carbon. The catalyst of this invention was prepared as described in Example 1.

The catalyst of Comparison A was prepared as follos: 100 g of activated carbon was calcined in an air atmosphere, first at 200° for two hours, then at 400° for two hours. The carbon was cooled, then sieved resulting in 54.0 g of calcined carbon, 20 mesh. A 0.076 g Re/ml solution was prepared by the addition of 5.0 g of $Re_2O_7$ to 50 ml of distilled water. Then, 19.7 ml of the solution, 10 ml of concentrated HCl, 50 ml of distilled water, 2.5 g of $PdCl_2$, and 50 g of the calcined carbon were added to a 1000 ml flask. After three hours with occasional stirring, the slurry was dried at 110° for eighteen hours. The Pd/Re/C catalyst was then reduced by the following procedure: heated at 150° in nitrogen for one hour, then at 150° in 50%/50% $N_2/H_2$ for one hour, then at 300° in 50%/50% $N_2H_2$ for three hours. After cooling, the catalyst was passivated in 1% $O_2/N_2$ atmosphere for three hours.

The catalyst of Comparison B was prepared as follows: 100 g of activated carbon was calcined in an air atmosphere, first at 200° for two hours, then at 400° for two hour. The carbon was cooled, then sieved resulting in 61.0 g mesh of calcined carbon, 20 mesh. A 0.076 g Re/ml solution was prepared by the addition of 5.0 g of $Re_2O_7$ to 50 ml of distilled water. Then, 19.7 ml of the solution was added to a 1000 ml flask and 50 g of the calcined carbon and 70 ml of distilled water were added. After four hours with occasional stirring, the slurry was dried at 110° for eighteen hours.

The Re/C material was reduced by the following method: heating at 150° in nitrogen for one hour, then at 150° in 50%/50% $N_2/H_2$ for one hour, then at 300° in 50%/50% $N_2H_2$ for three hours. The Re/C material was passivated in 1% $O_2/N_2$ for three hours. Next, 2.5 g of $PdCl_2$, 70 ml of distilled water, and 10 ml of concentrated HCl was charged into a 1000 ml flask. The Re/C material was added to the solution and the slurry was left at ambient temperature for three hours. The slurry was dried for eighteen hours at 110° and was reduced under the following conditions: heating at 150° in nitrogen for one hour, then at 150° in 50%/50% $N_2/H_2$ for one hour, then at 300° in 50%/50% $N_2/H_2$ for three hours. After cooling, the catalyst was passivated in 1% $O_2/N_2$ for three hours.

The hydrogenation was carried out as follows: in each case, the carbon-supported catalyst containing 3% Pd and 3% Re, weighing 18 g, was charged into a 0.37 inch diameter, Hastelloy C. high pressure reaction tube having a length of about two feet. The reaction tube was heated by a three-zone, electric, vertical furnace. A nitrogen purge of the reaction system was completed and the reactor was then pressured to 2500 psig with hydrogen. A steady hydrogen flow of 2 l/min, S.T.P., was continued while the reactor was slowly heated to the temperature at which the reaction was to take place and held for one hour to provide catalyst conditioning. When conditioning was complete, a 35 weight percent maleic acid solution was introduced at a given flow rate. The reactants were fed co-current, up-flow. Reaction products and excess hydrogen was discharged through a back-pressure regulating valve, with the reaction product sampled every half-hour.

The microstructure of the catalyst made by the process of Comparison A wherein Re and Pd are codeposited comprised Pd crystallites of only about 7 nm in average size and a highly dispersed Re phase. After use, Pd crystallites were larger and detected by X-ray dif- Then, 47.95 grams of the reduced Pd/C-Mg sample was added to 19 ml of 0.2M $Re_2O_7$ and 60 ml of distilled water. After three hours at room temperature, the slurry was dried at 110° C. for eighteen hours. The Pd/Re/C-Mg sample was then reduced as described above following the Pd addition and the reduced Pd/Re/C-Mg catalyst was passivated in 1.5% oxygen in nitrogen for eighteen hours. Passivated reduced Pd/Re/C-Mg catalyst was produced in the amount of 48.34 grams.

A catalyst comprising 3% Pd/3% Re/C containing 0.30 mole percent Ca (Example 53) was prepared as follows. First, 96.0 grams of the acid-leached carbon was added to a solution of 2.66 g of $CaCl_2$ in 150 ml of distilled water. After three hours at room temperature with occasional stirring, the slurry was dried, with frequent stirring, at 110° C. for eighteen hours. The Ca/C sample was calcined at 200° C. for two hours, then at 400° C. for an additional two hours. The resultant calcined, Ca/C sample was collected on a 20-mesh sieve.

The calcined Ca/C, 50.0 g, was added to a solution of 2.5 grams of $PdCl_2 + 10$ ml of concentrated HCl in 75 ml of distilled water. After three hours at room temperature, the slurry was dried, with frequent stirring, at 110° C. for eighteen hours. The Pd/C-Ca sample was then reduced by heating at 150° C. for one hour in 100 cc/min helium, then at 150° C. for one hour in 100 cc/min each of helium and hydrogen and finally at 300° C. for three hours in the flowing helium/hydrogen atmosphere. The sample was cooled to room temperature in flowing helium/hydrogen and then was passivated in 1.5% $O_2/N_2$ for eighteen hours.

Then, 49.0 grams of the reduced Pd/C-Ca sample was added to 19.35 ml of 0.2M $Re_2O_7$ and 65 ml of distilled water. After three hours at room temperature, the slurry was dried at 110° C. for eighteen hours. The Pd/Re/C-Ca sample was then reduced as described above following the Pd addition and the reduuced Pd/Re/C-Ca catalyst was passivated in 1.5% oxygen in nitrogen for eighteen hours. Passivated, reduced Pd/Re/C-Ca catalyst was produced in the amount of 50.28 grams.

A catalyst comprising 3% Pd/3% Re/C containing 0.30 mole percent K (Example 54) was prepared as follows. First, 96.0 grams of the acid-leached carbon was added to a solution of 1.38 of KOH in 150 ml of distilled water. After three hours at room temperature with occasional stirring, the slurry was dried, with frequent stirring, at 110° C. for eighteen hours. The K/C sample was calcined at 200° C. for two hours, then at 400° C. for an additional two hours. The resultant calcined, K/C sample was collected on a 20-mesh sieve.

The calcined K/C, 50.0 g, was added to a solution of 2.5 grams of $PdCl_2 + 10$ ml of concentrated HCl in 75 ml of distilled water. After three hours at room temperature, the slurry was dried, with frequent stirring, at 110° C. for eighteen hours. The Pd/C-K sample was then reduced by heating at 150° C. for one hour in 100 cc/min helium, then at 150° C. for one hour in 100 cc/min each of helium and hydrogen and finally at 300° C. for three hours in the flowing helium/hydrogen and then was passivated in 1.5% $O_2/N_2$ for eighteen hours.

Next, 48.4 grams of the reduced Pd/C-K sample was added to 19.10 ml of 0.2M $Re_2O_7$ and 65 ml of distilled water. After three hours at room temperature, the slurry was dried at 110° C. for eighteen hours. The Pd/Re/C-K sample was then reduced as described above following the Pd addition and the reduced Pd/Re/C-K catalyst was passivated in 1.5% oxygen in nitrogen for eighteen hours. Passivated, reduced Pd/Re/C-K catalyst was produced in the amount of 48.67 grams.

A catalyst comprising 3% Pd/3% Re/C containing 0.36 mole percent Li (Example 55) was prepared as follows. First, 96.0 grams of the acid-leached carbon was added to a solution of 1.17 grams of LiCl in 150 of distilled water. After three hours at room temperature with occasional stirring, the slurry was dried, with frequent stirring, at 110° C. for eighteen hours. The Li/C sample was calcined at 200° C. for two hours, then at 400° C. for an additional two hours. The resultant calcined, Li/C sample was collected on a 20-mesh sieve.

The calcined Li/C (50.0 grams) was added to a solution of 2.5 grams of $PdCl_2 + 10$ ml of concentrated HCl in 80 ml of distilled water. After three hours at room temperature, the slurry was dried, with frequent stirring, at 110° C. for eighteen hours. The Pd/C-Li sample was then reduced by heating at 150° C. for one hour in 100 cc/min helium, then at 150° C. for one hour in 100 cc/min each of helium and hydrogen and finally at 300° C. for three hours in the flowing helium/hydrogen atmosphere. The sample was cooled to room temperature in flowing helium/hydrogen and then was passivated in 1.5% $O_2/N_2$ for eighteen hours.

Then, 49.5 grams of the reduced Pd/C-Li sample was added to 19.5 ml of 0.2M $Re_2O_7$ and 60 ml of distilled water. After three hours at room temperature, the slurry was dried at 110° C. for eighteen hours. The Pd/Re/C-Li sample was then reduced as described above following the Pd addition and the reduced Pd/Re/C-Li catalyst was passivated in 1.5% oxygen in nitrogen for eighteen hours. Passivated, reduced Pd/Re/C-Li catalyst was produced in the amount of 49.97 grams.

These catalysts along with a catalyst made according to Example 48 and comprising 3% Pd/3% Re/C containing 0.5 mole percent Na (Example 56) were used in hydrogenation runs carried out as described in Examples 2 to 14 with reaction temperatures, reaction contact times and results shown in Table 11.

TABLE 11

| Example | Temperature °C. | Contact Time (Hrs) | Product//By-product THF/BDO//Aloh[1]/Suac[2] + Btyl[3] (Mol Percent) | Space Time Yield |
| --- | --- | --- | --- | --- |
| 52 | 180 | 1.4 | 23/40//3/34 | 268 |
|  | 200 | 1.4 | 37/53//9/1 | 411 |
|  | 200 | 2.2 | 38/45//16/<1 | 231 |
|  | 200 | 2.6 | 42/31//27/<1 | 199 |
| 53 | 180 | 2.0 | 34/57//7/2 | 266 |
|  | 180 | 1.4 | 12/18//2/68 | 143 |
|  | 200 | 1.0 | 31/28//5/36 | 336 |
|  | 200 | 1.4 | 35/47//6/12 | 402 |
|  | 215 | 2.0 | 65/22//11/1 | 231 |
|  | 215 | 1.0 | 46/27//8/19 | 414 |
|  | 215 | 1.4 | 61/23//15/1 | 372 |
| 54 | 180 | 1.4 | 25/52//4/19 | 313 |
|  | 180 | 2.0 | 28/66//6/<1 | 266 |
|  | 200 | 1.4 | 31/57//11/1 | 410 |
|  | 200 | 2.0 | 46/25//28/1 | 191 |
| 55 | 180 | 2.0 | 33/60//7/<1 | 257 |
|  | 180 | 1.9 | 33/61//6/<1 | 260 |
|  | 200 | 1.4 | 35/51//9/ 5 | 415 |
|  | 200 | 2.0 | 43/24//32/<1 | 200 |
|  | 215 | 1.9 | 74/2//25/ 0 | 194 |
| 56 | 180 | 2.4 | 55/18//4/23 | 176 |
|  | 190 | 2.2 | 77/8//15/<1 | 210 |
|  | 205 | 1.4 | 48/12//6/34 | 254 |
|  | 210 | 1.4 | 64/11//8/16 | 318 |

Hydrogenation was carried out using 27 g of this catalyst with a 35 weight percent aqueous solution of maleic acid at a temperature of 190° C., a $H_2$ pressure of 2500 psig (17 MPa), a contact time of 2.2 hours, and a hydrogen space time of 6.0 min. The reaction product in mol percent based on the carbon species was THF-55/BDO-34//monoalcohols8/γ-butyrolactone-3 and the spacetime yield was 240.

EXAMPLES 49 TO 51

A 3 weight percent Pd/3 weight percent Re/carbon-supported catalyst was prepared in the following manner: 100 g of Westates CC-521-G carbon was added to a solution of 9.6 g of $Na_2PdCl_4.3H_2O$ in 86 ml of distilled water. After one hour at room temperature, the slurry was dried with stirring via a steam bath. The carbon was impregnated with 4.0 g of NaOH in 88 ml of distilled water for two hours. The carbon was then washed with distilled water until chloride free; 150 g of the Pd on carbon sample was recovered following drying; and 45 g of the Pd on carbon was dried at 110° C. for 18 hrs. It was then heated; one hour at 150° C. in He flowing at 100 cc/min, followed by one hour at 150° C. in helium/hydrogen each at 100 cc/min; and finally, for three hours at 300° C. in the flowing helium/hydrogen atmosphere. After cooling under flowing helium/hydrogen, the sample was passivated with 1.5% oxygen in nitrogen for 18 hours. Then, 29.38 g of reduced Pd/C was added to a solution of 11.5 ml of 0.2M $Re_2O_7$ and 38.5 ml of distilled water. After three hours at room temperature, the slurry was dried at 110° C. for 18 hours. The resultant Pd/Re/C catalyst was reduced and passivated as above to give 29.44 g of catalyst.

Hydrogenation was carried out as in Examples 2 to 14 with the reaction temperatures and contact times shown in Table 9. The hydrogen pressure was 2500 psig (17 MPa) and the hydrogen spacetime was 6.0 min for all three Examples.

TABLE 9

| Example | Reaction Temperature °C. | Reaction Contact Time (Hrs) | Product//By-product THF/BDO//Aloh[1]/Btyl[2]/Suac[3] (Mol Percent) | Space Time Yield |
|---|---|---|---|---|
| 49 | 180 | 2.2 | 22/11//2/45/11 | 86 |
| 50 | 180 | 3.7 | 56/18//3.5/19/3 | 138 |
| 51 | 190 | 3.8 | 86/8//3.5/2/0.5 | 195 |

[1]Total monoalcohols:n-butanol, n-propanol
[2]γ-Butyrolactone.
[3]Succinic acid

COMPARISONS D TO H

Sequential Pd/Re Deposition Without Intermediate Reduction

A catalyst comprised of 3 weight percent of Pd and 3 weight percent of Re supported on carbon was prepared in the following manner. Carbon, 100 g, (Calgon PCB 12+30) was calcined at 200° C. for two hours, then at 400° C. for two hours. Then, 65.25 g of the carbon was recovered on a 20 mesh sieve. A sequential deposition of Pd and Re onto the recovered calcined carbon was made as follows: 50 g of the calcined carbon was added to a solution of 2.5 g of $PdCl_2$ and 10 ml of concentrated HCl in 75 ml of distilled water. After three hours at room temperature, with occasional stirring, the slurry was dried at 110° C. for eighteeen hours. One gram of the dried Pd/C sample was removed for analysis, and the remainder, 50.31 g, was added to 19.86 ml of a solution of 0.2M $Re_2O_7$ in 65 ml of distilled water. After three hours, with occasional stirring, at room temperature, the slurry was dried at 110° C. for eighteen hours. One gram of the dried Pd/Re/C sample was removed for analysis and the remainder was heated at 150° C. for one hour in 100 cc/min helium, then at 150° C. for one hour in 100 cc/min each of helium and hydrogen and then at 300° C. for three hours in the flowing He/$H_2$ atmosphere. The sample was then cooled to room temperature. The reduced Pd/Re/C sample was passivated in 1.5% oxygen in nitrogen for eighteen hours. The yield was 46.68 g of passivated, reduced Pd/Re/C catalyst.

Hydrogenation was carried out as in Examples 2 to 14 with the reduction temperatures, reaction contact times, and results shown in Table 10, said results showing incomplete conversions and poor selectivities.

TABLE 10

| Comparison | Reaction Temperature °C. | Reaction Contact Time (Hrs) | Product//By-product THF/BDO//Aloh[1]/Suac[2] + Btyl[3] (Mol Percent) | Space Time Yield |
|---|---|---|---|---|
| D | 180 | 2.0 | Succinic acid conversion was so low, reactor system plugged and no results were obtained. Highest Product pH prior to plugging = 2.0. | |
| E | 200 | 2.0 | 45/8//13/34 | 158 |
| F | 215 | 2.0 | 65/4//25/6 | 199 |
| G | 215 | 1.4 | 37/5//10/48 | 184 |
| H | 220 | 1.4 | 39/4//13/44 | 194 |

[1]Total monoalcohols: n-butanol, n-propanol.
[2]Succinic acid.
[3]γ-Butyrolactone.

EXAMPLES 52 TO 56

Carbon, 400 g (Calgon PCB 12×30) was added to 1M HCl. After 24 hours, the carbon was collected on a fritted funnel and then washed with distilled water until chloride-free. The acid treatment and washing were repeated and the carbon was then dried at 110° C. for 48 hours. The acid-washed carbon was recovered in the amount of 385.3 grams and subsequently used as follows.

A catalyst comprising 3% Pd/3% Re/C containing 0.30 mole percent Mg (Example 52) was prepared as follows. First, 96.0 grams of the acid-leached carbon was added to a solution of 4.82 g of $MgCl_2.6H_2O$ in 150 ml of distilled water. After three hours at room temperature with occasional stirring, the slurry was dried, with frequent stirring, at 110° C. for eighteen hours. The Mg/C sample was calcined at 200° C. for two hours, then at 400° C. for an additional two hours. The resultant calcined, Mg/C sample was collected on a 20-mesh sieve.

The calcined Mg/C, 50.0 g, was added to a solution of 2.5 grams of $PdCl_2$ + 10 ml of concentrated HCl in 75 ml of distilled water. After three hours at room temperature, the slurry was dried, with frequent stirring, at 110° C. for eighteen hours. The Pd/C-Mg sample was then reduced by heating at 150° C. for one hour in 100 cc/min helium, then at 150° C. for one hour in 100 cc/min each of helium and hydrogen and finally at 300° C. for three hours in flowing helium/hydrogen. The sample was cooled to room temperature in flowing helium/hydrogen and then was passivated in 1.5% $O_2/N_2$ for eighteen hours.

TABLE 11-continued

| Example | Temperature °C. | Contact Time (Hrs) | Product//By-product THF/BDO//Aloh[1] /Suac[2] + Btyl[3] (Mol Percent) | Space Time Yield |
|---|---|---|---|---|
| | 215 | 1.4 | 74/10//12/3 | 345 |

[1]Total monoalcohols: n-butanol, n-propanol.
[2]Succinic acid.
[3]γ-Butyrolactone.

We claim:

1. A method for making tetrahydrofuran, 1,4-butanediol or mixture thereof by hydrogenating a hydrogenating precursor in the presence of a solvent medium and a catalyst on a carbon support, said catalyst comprising about 0.5% to 10% of palladium and about 1% to 10% of rhenium by total weight of supported catalyst, the palladium being present in the form of crystallites having an average size of about 10 nm to 25 nm and the rhenium being present in the form of a highly dispersed phase of crystallites having an average size of less than about 2.5 nm.

2. A method according to claim 1 wherein the hydrogenatable precursor is selected from the group consisting of maleic acid, maleic anhydride, fumaric acid, succinic acid, malic acid, the esters corresponding to these acids, γ-butyrolactone and mixtures thereof.

3. A method according to claim 1 wherein the catalyst comprises about 1% to 6% of palladium and about 3% to 6% of rhenium by total weight.

4. A method according to claim 3 wherein the hydrogenatable precursor is selected from the group consisting of maleic acid, maleic anhydride, fumaric acid, succinic acid, malic acid, the esters corresponding to these acids, γ-butyrolactone and mixtures thereof.

5. A method according to claim 3 wherein the catalyst comprises about 3% palladium and about 3% of rhenium by total weight.

6. A method according to claim 5 wherein the hydrogenatable precursor is selected from the group consisting of maleic acid, maleic anhydride, fumaric acid, succinic acid, malic acid, the esters corresponding to these acids, γ-butyrolactone and mixtures thereof.

7. A method according to claim 1 wherein the rhenium crystallites have an average size of less than 1.5 nm.

8. A method according to claim 7 wherein the hydrogenatable precursor is selected from the group consisting of maleic acid, maleic anhydride, fumaric acid, succinic acid, malic acid, the esters corresponding to these acids, γ-butyrolactone and mixtures thereof.

9. A method according to claim 3 wherein the rhenium crystallites have an average size of less than 1.5 nm.

10. A method according to claim 9 wherein the hydrogenatable precusor is selected from the group consisting of maleic acid, maleic anhydride, fumaric acid, succinic acid, malic acid, the esters corresponding to these acids, γ-butyrolactone are mixtures thereof.

11. A method according to claim 5 wherein the rhenium crystallites have an average size of less than 1.5 nm.

12. A method according to claim 11 wherein the hydrogenatable precursor is selected from the group consisting of maleic acid, maleic anhydride, fumaric acid, succinic acid, malic acid, the esters corresponding to these acids, γ-butyrolactone and mixtures thereof.

13. A method for making tetrahydrofuran, 1,4-butanediol or mixtures thereof comprising hydrogenating a hydrogenatable precursor in the presence of a solvent medium and a catalyst comprising palladium and rhenium on a carbon support made by the method comprising, in sequence:

(i) impregnating the carbon support with a source of palladium, said palladium being in solution,
(ii) removing the solvent, and heating the palladium impregnated carbon at a temperature of about 150° C. to 550° C. under reducing conditions,
(iii) applying to the palladium impregnated carbon a source of rhenium that is in solution, and
(iv) removing the solvent.

14. A method according to claim 13 wherein the hydrogenatable precursor is selected from the group consisting of maleic acid, maleic anhydride, fumaric acid, succinic acid, malic acid, the esters corresponding to these acids, γ-butyrolactone and mixtures thereof.

15. A method for making tetrahydrofuran, 1,4-butanediol or mixtures thereof comprising hydrogenating a hydrogenatable precursor in the presence of a solvent medium and a catalyst on a carbon support, said catalyst comprising about 0.5% to 10% of palladium and about 1% to 10% of rhenium by total weight, made by the method comprising, in sequence:

(i) impregnating the carbon support with a source of palladium, said palladium being in solution,
(ii) removing the solvent and heating the palladium impregnated carbon at a temperature of about 150° C. to 550° C. under reducing conditions,
(iii) applying to the palladium impregnated carbon a source of rhenium that is in solution, and
(iv) removing the solvent.

16. A method according to claim 15 wherein the hydrogenatable precursor is selected from the group consisting of maleic acid, maleic anhydride, fumaric acid, succinic acid, malic acid, the esters corresponding to these acids, γ-butyrolactone and mixtures thereof.

17. A method according to claim 1 carried out at a reaction temperature of about 130° to 285° C., a hydrogen pressure of 2 MPa to 35 MPa, a hydrogen spacetime of about 1 to 10 minutes and a contact time of about 0.5 to 7 hours.

18. A method according to claim 1 carried out in aqueous solvent medium.

19. A method according to claim 15 carried out at a reaction temperature of about 130° to 285° C., a hydrogen pressure of 2 MPa to 35 MPa, a hydrogen spacetime of about 1 to 10 minutes and a contact time of about 0.5 to 7 hours 20. A method according to claim 15 carried out in aqueous solvent medium.

21. In a method for making tetrahydrofuran, 1,4-butanediol or mixtures thereof from an oxidizable maleic anhydride precursor comprising oxidizing the precursor to form maleic anhydride and reacting the maleic anhydride with hydrogen in the presence of a hydrogenation catalyst, the improvement which comprises:

(i) collecting the maleic anhydride from the oxidation step in water to form an aqueous solution of maleic acid, and
(ii) reacting the aqueous solution of maleic acid with hydrogen in the presence of a catalyst on a carbon support, said catalyst comprising about 0.5% to 10% of palladium and about 1% to 10% of rhenium by total weight, the palladium being present in the form of crystallites having an average size of about 10 nm to 25 nm and the rhenium being present in the form of a highly dispersed phase of crystallites having an average size of less than about 2.5 nm.

22. A method according to claim 21 carried out continuously.

23. In a method for making tetrahydrofuran, 1,4-butanediol or mixtures thereof from an oxidizable maleic anhydride precursor comprising oxidizing the precursor to form maleic anhydride and reacting the maleic anhydride with hydrogen in the presence of a hydrogenation catalyst, the improvement which comprises:
  (i) collecting the maleic anhydride from the oxidation step in water to form an aqueous solution of maleic acid, and
  (ii) reacting the aqueous solution of maleic acid with hydrogen in the presence of a catalyst on a carbon support, said catalyst comprising about 0.5% to 10% of palladium and about 1% to 10% of rhenium by total weight, made by the method comprising, in sequence:
    (a) impregnating the carbon support with a source of palladium, said palladium being in solution,
    (b) removing the solvent and heating the palladium impregnated carbon at a temperature of about 150° C. to 550° C. under reducing conditions,
    (c) applying to the palladium impregnated carbon a source of rhenium that is in solution, and
    (d) removing the solvent.

24. A method according to claim 23 carried out continuously.

25. A method for making tetrahydrofuran, 1,4-butanediol or mixtures thereof according to claim 23 comprising the additional step of (v) heating the catalyst composite of step (iv) at a temperature of about 150° C. under reducing conditions.

26. A method according to claim 25 carried out continuously.

27. A method according to claim 1 characterized by controlling the relative ratio of tetrahydrofuran to 1,4-butanediol by varying one or more variables selected from operating temperature, contact time and hydrogen spacetime.

28. A method according to claim 15 characterized by controlling the relative ratio of tetrahydrofuran to 1,4-butanediol by varying one or more variables selected from operating temperature, contact time and hydrogen spacetime.

29. A method according to claim 27 characterized by increasing the relative ratio of tetrahydrofuran to 1,4-butanediol by increasing one or more of the variables selected from operating temperature, contact time, and hydrogen spacetime.

30. A method according to claim 28 characterized by increasing the relative ratio of tetrahydrofuran to 1,4-butanediol by increasing one or more variables selected from operating temperature, contact time, and hydrogen spacetime.

* * * * *

UNITED STATES PATENT AND TRADEMARK OFFICE
CERTIFICATE OF CORRECTION

PATENT NO. : 4,550,185

DATED : October 29, 1985

INVENTOR(S) : Mabry et al.

It is certified that error appears in the above—identified patent and that said Letters Patent is hereby corrected as shown below:

Claim 1, lines 12-13, "hydrogenating precursor" should be --hydrogenatable precursor--.

Claim 10, line 58, "are mixtures" should be --and mixtures--.

Signed and Sealed this

Thirtieth Day of December, 1986

Attest:

DONALD J. QUIGG

Attesting Officer

Commissioner of Patents and Trademarks